United States Patent [19]

Kung et al.

[11] Patent Number: 5,278,286
[45] Date of Patent: Jan. 11, 1994

[54] IMMUNE INTERFERON

[75] Inventors: Hsiang-Fu Kung, Verona, N.J.; Hiromu Sugino, Hyogo; Susumu Honda, Takatsuki, both of Japan

[73] Assignee: Hoffmann-La Roche Inc., Nutley, N.J.

[21] Appl. No.: 16,610

[22] Filed: Feb. 19, 1987

Related U.S. Application Data

[60] Division of Ser. No. 639,551, Aug. 10, 1984, Pat. No. 4,681,930, which is a continuation-in-part of Ser. No. 534,040, Sep. 20, 1983, abandoned.

[51] Int. Cl.$^5$ .............................................. C07K 13/00
[52] U.S. Cl. .................... 530/351; 424/85.5; 435/811
[58] Field of Search ................ 530/351; 424/85, 85.5; 435/68, 811

[56] References Cited

U.S. PATENT DOCUMENTS

| | | | |
|---|---|---|---|
| 3,981,991 | 9/1976 | Stewart et al. | 424/85 |
| 4,017,600 | 4/1977 | Stewart et al. | 424/85 |
| 4,311,639 | 1/1982 | Ganfield et al. | 260/112.5 R |
| 4,341,761 | 7/1982 | Ganfield et al. | 424/85 |
| 4,361,509 | 11/1982 | Zimmerman et al. | 260/112 B |
| 4,388,234 | 6/1983 | Horecker | 260/112.5 R |
| 4,404,188 | 9/1983 | Donahoe et al. | 424/105 |
| 4,432,895 | 2/1984 | Tarnowski | 260/112 R |
| 4,476,049 | 10/1984 | Kung | 260/112 R |
| 4,485,017 | 11/1984 | Tan et al. | 210/635 |

FOREIGN PATENT DOCUMENTS 087686 9/1983 European Pat. Off.

OTHER PUBLICATIONS

Marglin & Meerifield *Ann Rev. Biochem* 39: 841–866 (1970).
Bonnerjea et al. *Bio/Technology* 4: 954–958 (1986).
Sofer & Britton *Biotechniques* 1(4), 198–203 (1983).
Goeddel et al., European Patent Application 0077670 (1983).
Ishida, European Patent Application No. 0083777 (1983).
Ishida, Australian Patent Application No. 48952/85 (1986).
Itoh et al., Australian Patent Application No. 25619/84 (1984).
Kikuchi et al., European Patent Application No. 0110044 (1984).
Lehninger, A., Biochemistry, Published by Worth Publishers, Inc., New York, N.Y., pp. 157–172, 1975.
Altrock et al., in the Biology of the Interferon System, 1983, De Maeyer, et al., Eds., Elsevier Science Publishers, New York, pp. 135–138.
De Chiara et al., European Patent Application Publication No. 128 467.
Goeddel et al., European Patent Application Publication No. 077 670.
Gray et al., European Patent Application Publication No. 146 354.
Hager et al., Anal. Biochem. 109:76 (1980).
Hatefi et al., Methods in Enzymology 34:770 (1974).
Kikuchi et al., European Patent Application Publication No. 110 044.
Livingston, Methods in Enzymology 34:723 (1974).
Prouty et al., J. Biol. Chem. 250:1112 (1975).

(List continued on next page.)

*Primary Examiner*—Robert J. Hill, Jr.
*Assistant Examiner*—Shelly Guest Cermak
*Attorney, Agent, or Firm*—George M. Gould; George W. Johnston; William Krovatin

[57] ABSTRACT

An intact human immune interferon protein and a method for the extraction and purification of intact recombinant human immune interferon is disclosed. This method permits the purification to homogenity of intact recombinant human immune interferon.

3 Claims, 5 Drawing Sheets

OTHER PUBLICATIONS

Rehberg et al., J. Biol. Chem. 257:11497 (1982).
Staehelin et al., J. Biol. Chem 256:9750 (1981).
Staehelin et al., Proc. Natl. Acad. Sci. USA 78:1848 (1981).
Tarnowski; Pharm. Tech., Feb. 1983, pp. 70–79.
Tsukamoto et al., European Patent Application Publication No. 103 898.
Ullmann et al., Biochem. Biophys. Res. Commun. 35:35 (1969).
Wetzel et al., Biochemistry 19:6096 (1980).
Wetzel et al., Gene 16:63 (1981).
Braude, European Patent Application Publication No. 063 482 A2.
Fiers, European Patent Application Publication No. 088 540 A2.
Goeddel et al., European Patent Application Publication No. 077 670.
Gray et al., Nature 295:503 (1982).
Gray et al., European Patent Application Publication No. 146 354 A2.
Hochkeppel et al., Nature 296:258 (1982).
Kikuchi et al., European Patent Application Publication No. 89676A2.
Kung et al., Methods in Enzymology 119:204 (1986).
Secher et al., Nature 285:446 (1980).
Yep et al., Proc. Natl. Acad. Sci., vol. 79, pp. 1820–1824, 1982.

FIG. IA
REDUCING SDS-PAGE

FIG. IB
NON-REDUCING SDS-PAGE

FIG. 2

AGGAGGAATTC ATG TGT TAC TGC CAG GAC CCA TAT GTA AAA GAA GCA
            MET Cys Tyr Cys Gln Asp Pro Tyr Val Lys Glu Ala

GAA AAC CTT AAG AAA TAT TTT AAT GCA GGT CAT TCA GAT GTA GCG GAT
Glu Asn Leu Lys Lys Tyr Phe Asn Ale Gly His Ser Asp Val Ala Asp

AAT GGA ACT CTT TTC TTA GGC ATT TTG AAG AAT TGG AAA GAG GAG AGT
Asn Gly Thr Leu Phe Leu Gly Ile Leu Lys Asn Trp Lys Glu Glu Ser

GAC AGA AAA ATA ATG CAG AGC CAA ATT GTC TCC TTT TAC TTC AAA CTT
Asp Arg Lys Ile MET Gln Ser Gln Ile Val Ser Phe Tyr Phe Lys Leu

TTT AAA AAC TTT AAA GAT GAC CAG AGC ATC CAA AAG AGT GTG GAG ACC
Phe Lys Asn Phe Lys Asp Asp Gln Ser Ile Gln Lys Ser Val Glu Thr

ATC AAG GAA GAC ATG AAT GTC AAG TTT TTC AAT AGC AAC AAA AAG AAA
Ile Lys Glu Asp MET Asn Val Lys Phe Phe Asn Ser Asn Lys Lys Lys

CGA GAT GAC TTC GAA AAG CTG ACT AAT TAT TCG GTA ACT GAC TTG AAT
Arg Asp Asp Phe Glu Lys Leu Thr Asn Tyr Ser Val Thr Asp Leu Asn

GTC CAA CGC AAA GCA ATA CAT GAA CTC ATC CAA GTG ATG GCT GAA CTG
Val Gln Arg Lys Ala Ile His Glu Leu Ile Gln Val MET Ala Glu Leu

TCG CCA GCA GCT AAA ACA GGG AAG | CGA AAA AGG AGT CAG ATG
Ser Pro Ala Ala Lys Thr Gly Lys | Arg Lys Arg Ser Gln MET
                         15K

CTG TTT CGA GGT CGA AGA GCA TCC CAG | TAA
Leu Phe Arg Gly Arg Arg Ala Ser Gln |
                              18k

FIG. 3
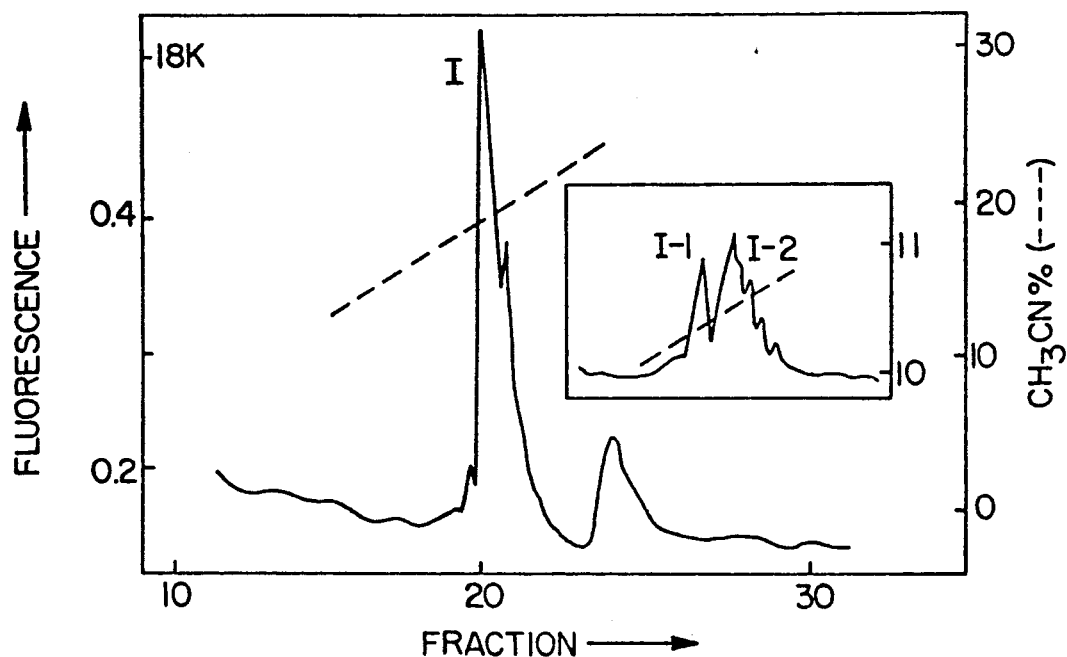
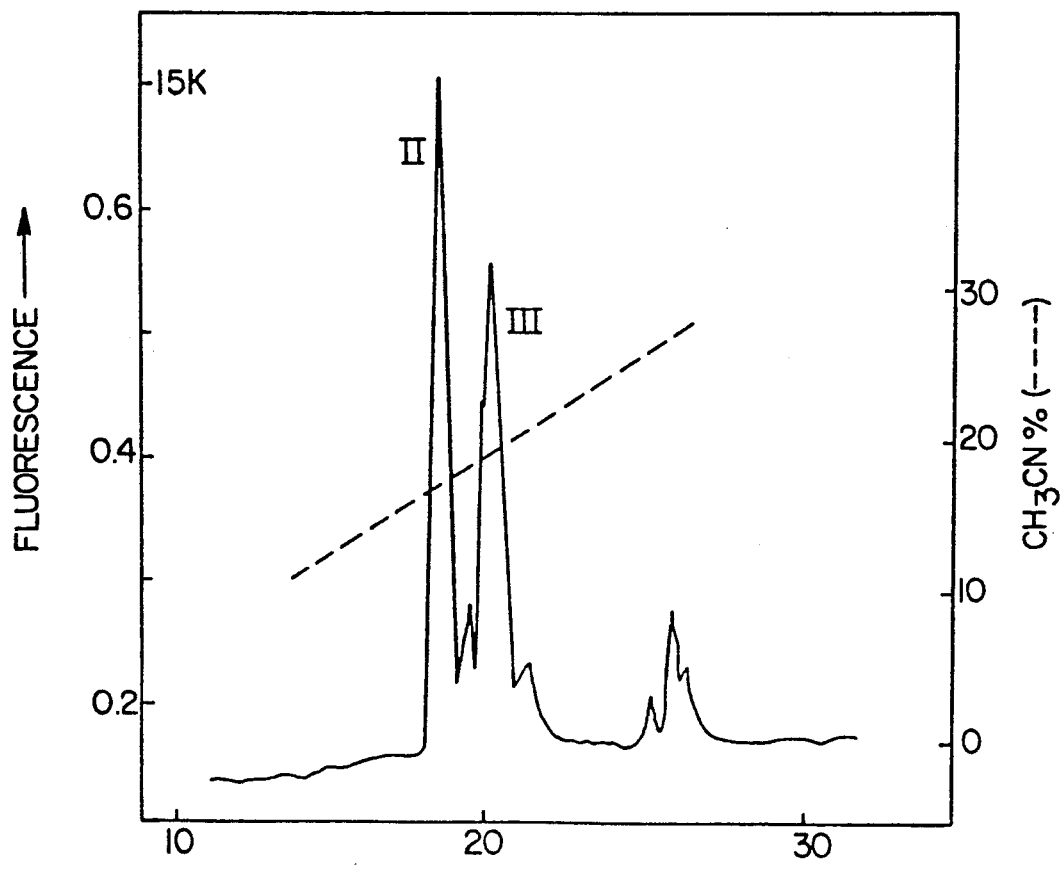

ముMMUNE INTERFERON

IMMUNE INTERFERON

This is a division of application Ser. No. 639,551 filed Aug. 10, 1984, now U.S. Pat. No. 4,681,930 which is a continuation-in-part of U.S. patent application Ser. No. 534,040, filed Sep. 20, 1983, now abandoned.

FIELD OF THE INVENTION

This invention relates to recombinant human immune interferon and a method for its extraction and purification from a microorganism preparation which contains this protein.

BRIEF DESCRIPTION OF THE FIGURES

FIG. 3 illustrates the separation of C-terminal CNBr peptides of the 15K and 18K rIFN-γ.

BACKGROUND OF THE INVENTION

Figure 1:
FIG. 1A and 1B illustrate sodium dodecyl sulfate-polyacrylamide gel electrophoresis of purified recombinant human immune interferon in photo "A" reducing condition (0.7M-beta-mercaptoethanol in the sample loading buffer) and in "B" in non-reducing condition.

The prior art has devised various methods for effecting the extraction and purification of the family of anti-viral proteins known as interferon. To date there are three major classes of interferon: IFN-alpha (leukocyte), IFN-beta (fibroblast) and IFN-γ (immune). Although the various interferon classes may be related in terms of anti-viral, anti-proliferative or structural arrangement, the prior art has so far been unable to devise a uniform method for the extraction and purification of all of these classes. Indeed, many of the processes useful for the extraction and purification of leukocyte interferon from a crude mixture of other proteins and cell debris would not work to extract and purify out fibroblast or immune interferon from the same kind of preparation.

The extraction step in purification processes of the prior art typically involved either the mechanical (i.e., sonication) or chemical lysis of microorganisms which have produced, often through recombinant techniques, the desired foreign protein. However, during this mechanical or chemical lysis procedure various cellular proteases are also released into the mixture. These proteases are then free to enzymatically act upon and degrade the foreign protein in the mixture. These proteases can, therefore, hinder or inhibit the purification to homogeneity of the complete or mature and biologically active form of the foreign protein by degrading the foreign proteins.

It is, therefore, an object of the present invention to provide a method which overcomes the limitations of the prior art extraction and purification techniques whereby the intact sequence form of immune interferon is present and whereby proteolytic fragments are eliminated from the purified immune interferon preparation.

It is further an object of the present invention to obtain a homogeneous and intact form of immune interferon.

SUMMARY OF THE INVENTION

Broadly stated, this invention comprises intact human immune interferon protein and a method for extracting and purifying the immune interferon from microorganisms wherein the extraction is performed with an anti-proteolytic reagent, such as guanidine-HCl, which inhibits protease or enzyme activity and which does not affect the biological activity of the immune interferon and wherein the purification step utilizes novel monoclonal antibodies to immune interferon.

DESCRIPTION OF THE PREFERRED EMBODIMENTS

It has now been discovered in the case of immune interferon, that extraction and purification with any of the conventional techniques described in the prior art will not yield an entirely homgeneous preparation of immune interferon with an intact or complete amino acid sequence. Only recently has recombinant technology advanced to the point at which it is possible to obtain sufficient quantities of rINF-γ so as to characterize it and determine its amino acid sequence. When conventional prior art techniques were utilized to extract rINF-γ preparations and the amino acid sequence of purified material was determined, it was discovered that the purified preparation was, in fact, comprised of a variety of related protein species of different molecular weight. It has further now been discovered by amino acid sequencing that these proteins species are actually the intact sequence form of immune interferon in combination with a majority of fragments of the intact sequence protein. Surprisingly, even though it has now been discovered that the prior art mixture contained both intact immune interferon protein and fragments thereof, it has been discovered that apparently a component of this mixture has also retained biological activity.

The extraction of rIFN-γ can be carried out with the use of sonification or chemical lysis. However, the rIFN-γ (the DNA base sequence and amino acid sequence deduced therefrom of which is described in reference 1) is degraded during the sonification or chemical lysis extraction step. Sonification of frozen cells however, yielded primarily the product (15K rIFN-γ, i.e., removal of C-terminal amino acid residues No. 132–146). This degradation can be prevented with the use of a reagent for extraction, such as guanidine-HCl, which does not affect the biological activity or amino acid sequence of the rIFN-γ under the conditions of extraction. Additionally, it has surprisingly been found that immune interferon retains its biological activity after a guanidine-HCl extraction step even though guanidine-HCl destroys the biological activity when added to a purified preparation of immune interferon.

This invention, therefore, comprises an intact and complete sequence form of recombinant human immune interferon. This protein is obtained from a preparation of transformed microorganisms containing it by treating the transformed microorganisms with a reagent (or mixture of reagents), such as guanidine-HCl, a protein denaturing agent, which, it is believed, inhibits protease or enzyme activity concurrently with extraction and which does not affect the activity of the desired protein under the conditions of extraction. Purified rIFN-γ is finally obtained by applying the extraction supernatant, preferably after appropriate dilution, directly on a purification means, preferably a monoclonal antibody column. These extraction and purification processes can also be automated for large-scale production. Thus, the invention makes possible for the first time the availability of large amounts of homogenous rIFN-γ and thus will permit extensive clinical trials, biological studies, X-ray crystallography and structure-function studies.

The anti-proteolytic agent of this invention may be any guanidinium salt. Among such guanidinium salts there are included the organic acids such as for example acetic acid and the mineral acids such as for example the hydrohalides, i.e. hydrobromide, hydrochloride, hydrofluoride and hydroiodide.

The preferred guanidinium salt is guanidine hydrochloride. The concentration of guanidinium salt in the treatment of the microorganisms is not critical in that any effective amount may be used. It is preferred, however, that a 3 to 7M solution of the guanidinium salt be used for treating the microorganisms and that about 3 to 9 volumes of the salt solution be used per gram of transformed microorganisms. The concentration of the salt may be achieved by making the salt up in a solvent such as water or aqueous buffers, such as ammonium acetate, pyridine acetic acid, sodium borate, and the like. It is also foreseeable that in the practice of this invention other protease inhibitor reagents may be used, such as urea and thiocyanate.

Further preferred embodiments will be illustrated in the following specification and examples.

Recombinant human immune interferon (rIFN-γ) produced in *E. coli* is preferably extracted from frozen cell paste by 7M guanidine-HCl and purified by purification means preferably with a novel monoclonal antibody affinity column using 0.5-5M guanidine or 30-70% ethylene glycol as eluent. The purified interferon with an apparent M.W. of 18,000 daltons (18K) on sodium dodecyl sulfate-polyacrylamide gel electrophoresis has been obtained with guanidine extraction, whereas lower M. W. species (major species about 15,000 daltons) were isolated by sonification in the absence of guanidine. The amino terminal sequences of both the 18K and 15K proteins were consistent with the sequence predicted from the DNA coding for this human immune interferon protein. The DNA sequence of 18K immune interferon as used throughout this specification has the following formula:

```
         X
AGGAGGAATTC ATG TGT TAC TGC CAG GAC CCA TAT GTA AAA GAA GCA

GAA AAC CTT AAG AAA TAT TTT AAT GCA GGT CAT TCA GAT GTA GCG

GAT AAT GGA ACT CTT TTC TTA GGC ATT TTG AAG AAT TGG AAA GAG

GAG AGT GAC AGA AAA ATA ATG CAG AGC CAA ATT GTC TCC TTT TAC

TTC AAA CTT TTT AAA AAC TTT AAA GAT GAC CAG AGC ATC CAA AAG

AGT GTG GAG ACC ATC AAG GAA GAC ATG AAT GTC AAG TTT TTC AAT

AGC AAC AAA AAG AAA CGA GAT GAC TTC GAA AAG CTG ACT AAT TAT

TCG GTA ACT GAC TTG AAT GTC CAA CGC AAA GCA ATA CAT GAA CTC

ATC CAA GTG ATG GCT GAA CTG TCG CCA GCA GCT AAA ACA GGG AAG

CGA AAA AGG AGT CAG ATG CTG TTT CGA GGT CGA AGA GCA TCC CAG TAA
                                                               Y
``` wherein the nucleotides under the "X" code for the ribosome binding site and protein translational start signal, the nucleotides over "Y" code for the translational stop signal and the nucleotides in between "X" and "Y" code for the 18K immune interferon protein.

The C-terminal sequence which was determined by analyzing and sequencing purified C-terminal peptide released from the 18K rIFN-γ matched with the predicted amino acid sequence or rIFN-γ indicating that the 18K species is the intact molecule. The amino acid sequence of 18K immune interferon as used throughout this specification has the following formula:

| X'- | | | | | | | | | | | |
|---|---|---|---|---|---|---|---|---|---|---|---|
| Cys | Tyr | Cys | Gln | Asp | Pro | Tyr | Val | Lys | Glu | Ala | Glu |
| Asn | Leu | Lys | Lys | Tyr | Phe | Asn | Ala | Gly | His | Ser | Asp |
| Val | Ala | Asp | Asn | Gly | Thr | Leu | Phe | Leu | Gly | Ile | Leu |
| Lys | Asn | Trp | Lys | Glu | Glu | Ser | Asp | Arg | Lys | Ile | Met |
| Gln | Ser | Gln | Ile | Val | Ser | Phe | Tyr | Phe | Lys | Leu | Phe |
| Lys | Asn | Phe | Lys | Asp | Asp | Gln | Ser | Ile | Gln | Lys | Ser |
| Val | Glu | Thr | Ile | Lys | Glu | Asp | Met | Asn | Val | Lys | Phe |
| Phe | Asn | Ser | Asn | Lys | Lys | Lys | Arg | Asp | Asp | Phe | Glu |
| Lys | Leu | Thr | Asn | tyr | Ser | Val | Thr | Asp | Leu | Asn | Val |
| Gln | Arg | Lys | Ala | Ile | His | Glu | Leu | Ile | Gln | Val | Met |
| Ala | Glu | Leu | Ser | Pro | Ala | Ala | Lys | Thr | Gly | Lys | Arg |
| Lys | Arg | Ser | Gln | Met | Leu | Phe | Arg | Gly | Arg | Arg | Ala |
| Ser | Gln | | | | | | | | | | |

It is also within the contemplation of this invention that the amino termines of the immune interferon protein could begin with a methionine (met) at position X', begin without a methionone or comprise a mixture thereof.

In a preferred embodiment of this invention, the microorganism employed as the recipient in the fermentation procedures and unless otherwise noted, is the microorganism *Escherichia coli* K-12 strain 294 as described in British Patent Publication No. 2055382A and which is incorporated by reference herein. This microorganism has been deposited with the American Type Culture Collection, ATCC Accession No. 31446, deposited Oct. 28, 1978. Furthermore, all recombinant DNA work herein was performed in compliance with applicable guidelines of the National Institutes of Health.

The invention, in its most preferred embodiments, is described with reference to E. coli, including not only E. coli K-12 strain 294, defined above, but also other known E. coli strains such as E. coli MA210 or RR1 (ATCC #31343), or other microbial strains many of which are publicly available or deposited and available from recognized microorganism depository institutions, such as the American Type Culture Collection (ATCC)-cf. the ATCC catalog listing.

E. coli RR1 (pRK248cI$_{ts}$, pRC231/IFN-γ) (the construction of this recombinant organism is detailed in the co-pending case U.S. Ser. No. 397,388, filed Jul. 12, 1982, Crowl-inventor, and which is incorporated by reference herein) was used in the following examples for rIKF-γ fermentations. The pRK248cI$_{ts}$ and pRC231/IFN-γ plasmids contained temperature sensitive repressor and IFN-γ gene respectively. Expression of rIFN-γ gene was under the control of P$_L$ promoter.

Overnight cultures of E. coli RR1 (pRK248cI$_{ts}$, pRC231/IF-γ) (See copending U.S. patent application No. 397,388 filed Jul. 12, 1983 for preparation of this E. coli strain) were grown in LB broth at 30° C. One liter of the overnight culture was diluted to 10 liters with minimal M-9 medium containing casamino acids. At logarithmic growth, the culture was shifted from 30° C. to 42° C. and continued to grow at 42° C. for 2-3 hours. Bacteria were harvested by centrifugation and the bacterial pellets were stored at −20° C. until used. All fermentations and procedures were performed in accordance with recombinant DNA guidelines of the National Institutes of Health.

Iodo [1-$^{14}$C] acetic acid was obtained from New England cyanogen bromide from Pierce Inc., carboxypeptidase A from Sigma Inc., fluorescamine from Hoffmann-La Roche Inc., C-8 and C-18 reverse-phase chromatographic columns from Supelco Inc. All the solvents used for protein characterization were re-distilled over ninhydrin.

Carboxymethylation of rIFN-γ by $^{14}$C-iodoacetic acid was carried out in the presence of 6M guanidine HCl as described in published procedures of reference (3). Excess reagent was removed by HPLC on C8 reverse-phase column. Carboxypeptidase digestion was performed in 0.2M NH$_4$HCO$_3$ as described in reference (4).

The rIFN-γ was treated with CNBr (100-fold molar excess over methionine) in 70 percent formic acid as described in reference (5). CNBr peptides were separated by HPLC on a C-18 reverse-phase column. A linear gradient of 0 to 70 percent of CH$_3$CN in 0.1% trifluoroacetic acid was used for peptide elution.

Protein or peptide samples were hydrolyzed for 20-24 hours in sealed, N$_2$-flushed, evacuated tubes in constant boiling HCl containing 4% thioglyolic acid. Amino acid analyses were performed using a fluorescamine amino acid analyzer as described in reference (6).

An ABI (Applied Biosystems, Inc.) gas-phase sequencer 470A was used for sequence analyses of carboxymethylated proteins as described in reference (7). Samples of PTH-amino acids were identified by reverse-phase HPLC on an ultrasphere ODS column as described in reference (8).

As used herein the term "interferon activity" refers to the characteristic antiviral and antigrowth activity characteristic of the interferons. The characteristic antiviral activity of rIFN can be determined using the cytophatic effect inhibition test described in Familleti, P.C. et al., Methods in Enzymology 78, 387(1981). The characteristic antigrowth activity of rIFN can be determined using the procedure described in Evinger, M. & Pestka, S., Methods in Enzymology, 79, 45 (1981).

Monoclonal antibodies were made against a synthetic polypeptide of the last 16 amino acid residues of the C-terminal peptide of rIFN-γ. One of the monoclonal antibodies (Mo γ 2–11.1) was used for the purification of rIFN-γ. More specifically, the monoclonal antibodies and antibody affinity column of this invention were prepared as described in co-pending patent application PCT/JP83/00174, filed May 31, 1983 in Japan and U.S. application No. 534,091 filed Sep. 20, 1983 and as described below in the following examples.

EXAMPLE 1

Synthesis of carrier protein-polypeptide complex used as antigen

The polypeptide H-Lys-Arg-Lys-Art-Ser-Gln-Met-Leu-Phe-Arg-Gly-Arg-Arg-Ala-Ser-Gln-OH was coupled with thyroglobulin (hereinafter, TG) according to the method of Goodfriend et al. (Science, 144, 1334, 1964). The above mentioned peptide can be produced by the conventional methods of peptide synthesis. Either of the solid phase method and liquid phase method may be used, although the liquid phase synthetic method is advantageous in many cases. Such methods of peptide synthesis are described, for example, by Schroder and Lubke in "The Peptides", vol. 1, Academic Press, New York, U.S.A., 1966, or by Izumiya et al. in "Peptide Synthesis", Maruzen, Tokyo, Japan, 1975, or by Haruaki Yajima in "Experiments in Biochemistry, vol. 1, pages 207–400", Tokyo Kagaku Dojin, 1977, and include, among others, the azide method, chloride method, acid anhydride method, mixed acid anhydride method, DCC method, active ester method, method using Woodward reagent K, carbodiimidazole method, oxidation/reduction method and DCC/additive (e.g. HONB, HOBt, HOSu) method.

Said peptide can be produced by condensing a reactive carboxyl-containing starting material corresponding to one of the two fragments resulting from division of said peptide at any site of the peptide bonding thereof with a reactive amino-containing starting material corresponding to the other fragment by any of the conventional peptide synthesis methods and, in case the condensation product has a protective group, eliminating the protective group in the conventional manner.

The method of protecting a functional group which should not be involved in the reaction between the materials, the protective group to be used in such protection, the method of eliminating such protective group and the method of activating the functional group to be involved in the reaction, for instance, can be selected adequately from among known ones or means.

Thus, 2.5 mg of said polypeptide was mixed with 3.75 mg of TG and, following addition of 2 ml of 50 mM phosphate buffer, the mixture was stirred well in ice water. Thereto was gradually added drop by drop a solution of 30.4 mg of carbodiimide hydrochloride in 200 ml of distilled water. Thereafter, the mixture was stirred in ice water for 3 hours. After the reaction, dialysis was performed against distilled water to a sufficient extent, followed by lyophilization to give 4.7 mg of a protein complex.

EXAMPLE 2

Preparation of antigen for Enzyme Immunoassay (EIA) for antibody detection

The antigen for EIA was prepared according to Kitagawa et al. (Journal of Biochemistry, vol. 79, page 233, 1976).

(i) Introduction of a maleimido group into the polypeptide

The polypeptide complex (350 nmoles) of Example 1 was dissolved in 1 ml of 100 mM phosphate buffer (pH 6.8), and the solution was added to a solution of 585 ug (1.75 umoles) or N-(4-carboxycyclohexylmethyl)maleimide N-hydroxy-succinimide ester in 70 ul of N,N-dimethylformamide. The mixture was stirred at 30° C. for 30 minutes. After the reaction fractionation was performed using a Sephadex G-25 column to give 185 nmoles of a polypeptide fraction with the maleimido group introduced therein.

(ii) Coupling of the maleimido-group-containing polypeptide with beta-D-galactosidase The maleimido-containing polypeptide (16.5 nmoles) as obtained in Example 2 (i) was mixed with 3.3 nmoles or beta-D-galactosidase. After 18 hours of reaction at 4° C., 412,5 nmoles of beta-mercaptoethanol was added for teminating the reaction. The beta-D-galactosidase-coupled polypeptide was fractionated on a Sepharose 6B column and used for the subsequent experiments.

EXAMPLE 3

Immunization

Each of female BALB/C mice aged 7 to 8 weeks was subcutaneously inoculated with 40 ug (on the protein basis) or the protein complex obtained in Example 1 (as the antigen) in intimate admixture with Freund's complete adjuvant (primary immunization). Two weeks after the primary immunization, the mice were subcutaneously inoculated with the antigen at the same dose as above in intimate admixture with Freund's incomplete adjuvant (secondary immunization). Further two weeks later, a third immunization was made in the same manner as in the secondary immunization. Six days after the third immunization, partial blood sampling was made from the mice and the serum antibody titers were determined by the EIA method described in *Immunopharmacology*, 1:3 (1978). The mouse numbered γ-2 gave the highest antibody titer and was subjected to the final immunization by intravenous inoculation with 120 ug of the antigen dissolved in 0.5 ml of aqueous sodium chloride. The antibody titer data for each mouse are shown in Table 1.

TABLE 1

| | Antipeptide antibody titers in immunized mice | | |
|---|---|---|---|
| | B/T (%) | | |
| Mouse No. | Primary immunization[1] | Secondary immunization[2] | Third immunization[3] |
| γ-1 | —[4] | N.D | 24.5 |
| 2 | N.D[5] | 19.3 | 35.3 |
| 3 | — | N.D | 24.7 |
| 4 | N.D | 1.3 | 1.7 |

TABLE 1-continued

| | Antipeptide antibody titers in immunized mice | | |
|---|---|---|---|
| | B/T (%) | | |
| Mouse No. | Primary immunization[1] | Secondary immunization[2] | Third immunization[3] |
| 5 | N.D | 1.8 | 5.0 |
| 6 | — | N.D | 0.8 |
| Normal mouse | 0.6 | 0.1 | N.D |

[1] Serum dilution ratio: 1/1000
[2] Serum dilution ratio: 1/6300
[3] Serum dilution ratio: 1/7800
[4] —: Not detectable
[5] ND: Not determined
B/T: (Bound enzyme activity/total added enzyme activity) × 100

EXAMPLE 4

Cell fusion

Immunization was performed by the method described in Example 3. Three days after the final immunization, the spleen was excised from the γ-2 mouse, filtered under pressure through a stainless mesh, and suspended in Eagle's minimum essential medium (MEM) to give a spleen cell suspension. For cell fusion, BALB/C mouse-derived P3-x63.Ag8.U1 (P3U1) myeloma cells were used (Current Topics in Microbiology and Immunology, vol. 81, page 1, 1978). Cell fusion was performed by the original method (Nature, vol. 256, page 495, 1975). Thus, spleen cells and P3U1 cells were separately washed three times with serum-free MEM and mixed at a ratio of 5:1 (in number of cells). The mixture was centrifuged at 800 rpm for 15 minutes, whereby the cells were settled. After thorough removal of the supernatant, the sediment was lightly loosened, 0.3 ml of 45% polyethylene glycol (PEG) 6000- (Koch-Light) was added, and the mixture was allowed to stand in a warm water tank maintained at 37° C. for 7 minutes so as to effect cell fusion. Thereafter, MEM was added thereto at a rate of 2 ml per minute. After addition of 12 ml in total of MEM, the resulting mixture was centrifuged at 600 rpm for 15 minutes, followed by removal of the supernatant. The cell sediment was suspended in RPMI-1640 medium supplemented with 10% fetal calf serum (RPMI1640-10FCS) in a concentration of $2 \times 10^5$ P3U1 cells/ml and each of 144 wells on 24-well multidishes (Linbro) was seeded with 1 ml of the suspension. After seeding, the cells were incubated at 37° C. in a 5% carbon dioxide gas incubator. After 24 hours, HAT-selective culture was started by adding RPMI1640-10FCS medium supplemented with HAT ($1 \times 10^{-4}$M hypoxanthine, $4 \times 10^{-7}$M aminopterin, $1.6 \times 10^{-5}$M thymidine) (HAT medium) in an amount of 1 ml per well. The HAT-selective culture was continued while 1 ml of the old medium was replaced by 1 ml of HAT medium 3, 5 and 7 days after start of the culture. The growth of hybridomas was noted 10 to 14 days after cell fusion. When the culture broth turned yellow (about $1 \times 10^6$ cells/ml), the supernatant was collected and examined for the presence of antibody by the EIA method. In this manner, supernatants from 141 wells in which hybridoma growth had been noted were examined. Two wells (γ 2-11 γ and 2-100) afforded intense antibody activity and other two wells (γ 2-62 and γ 2-70) presented weak antibody activity.

EXAMPLE 5

Cloning

Hybridomas from 3 wells (gamma 2-11, 62 and 100) which were positive in antibody activity were cloned by the limiting dilution method. Thus, hydribdoma cells were suspended in RPMI1640-20FCS in a concentration of at least about 2 hybridoma cells/ml and the suspension was distributed in 0.1-ml portions into the wells on a 96-well microplate (Nunc). In said distribution, $5 \times 10^5$ per well of BALB/C mouse thymocytes were added as feeder cells. As a result, cell proliferation was observed in about 2 weeks. The supernatant was then collected and examined for the presence of antibodies by the EIA method as described in Example 4. Antibody activity was noted in 8 out of 19 clones from γ 2-11 well, in 3 out of 54 clones from γ 2-62 well, and in 5 out of 47 clones from γ 2-100 well (Table 2).

TABLE 2

| Anti-peptide antibody activity of cloned hybridomas | |
|---|---|
| Hybridoma No. | B/T (%) |
| _γ2-11_ | |
| 1 | 68 |
| 2 | 31 |
| 3 | 63 |
| 6 | 68 |
| 7 | 67 |
| 9 | 69 |
| 12 | 42 |
| 18 | 60 |
| _γ2-62_ | |
| 14 | 20 |
| 16 | 21 |
| 34 | 16 |
| _γ2-100_ | |
| 2 | 69 |
| 3 | 70 |
| 16 | 56 |
| 25 | 80 |
| 46 | 33 |
| Hyperimmune mouse serum | 35 |

EXAMPLE 6

Binding capacity of monoclonal antibody to IFN-γ

The binding capacity of monoclonal antibody to IFN-γ was determined by the following method. To 300 ul of a 3% solution of cellulose coupled with rabbit anti-mouse IgG antibody, 300 ul of the culture supernatant for each of 2 or 3 cloned cell lines from each of γ 2-11, 2-62 and 2-100 wells was added, and the reaction was allowed to proceed at room temperature for 12 to 20 hours. Thereafter, the cellulose was thoroughly washed with physiological saline, and 550 U/ml of IFN-γ obtained by the procedure mentioned below was added thereto. After 3 to 4 hours of reaction, the supernatant was collected and the IFN-γ obtained by the procedure mentioned below was added thereto. After 3 to 4 hours of reaction, the supernatant was collected and the IFN-γ activity therein was determined by the cytopathic effect (CPE) reading method using a microplate (Applied Microbiology, vol. 16, page 1706, 1968). Thus, 50 ul of MEM was placed in each well of a 96-well microplate (Nunc) and 50 ul of a WISH cell suspension ($4 \times 10^5$ cells/ml) in 20% FCS-containing MEM was added, and incubation was conducted in a carbon dioxide gas incubator at 37° C. About 35 hours later, when cells in the IFN sample-free well showed 100% CPE, each well was microscopically observed for the estimation of CPE, and the reciprocal of the dilution factor for the IFN sample in that well in which 50% CPE was noted was referred to as the IFN titer.

The IFN-γ sample used was the supernatant collected 72 hours after stimulation of human peripheral lymphocytes with 40 ug/ml of concanavalin A and 15 ng/ml of 12-0-tetra-decanoylphorbol-13-acetate. Each ml of this culture supernatant contained 4400 units of human IFN-γ (acid-labile and unstable to pH treatment). If antibodies having binding capacity to IFN-γ are present in the cloned cell culture supernatant, then the added IFN-γ should be conjugated to the antibodies on cellulose and reduction in IFN-γ activity of the supernatant should occur. As a result, for the clone γ 2-11, relatively intense binding activity to IFN-γ was noted and 50–75% of the added IFN-γ (550 U/ml) was conjugated to antibodies (Table 3).

TABLE 3

| Absorption of IFN-γ activity by monoclonal antibodies | | |
|---|---|---|
| Hybridoma | Remaining IFN activity (U/ml) | |
| culture supernatant | Experiment 1 | Experiment 2 |
| γ2 - 11.1 | 138 | 275 |
| γ2 - 11.2 | 207 | N.D. |
| γ2 - 11.6 | N.D. | 275 |
| γ2 - 62.2 | 275 | 550 |
| γ2 - 62.3 | 275 | 550 |
| γ2 - 100.2 | 550 | N.D. |
| γ2 - 100.3 | 550 | N.D. |
| — | 550 | 550 |

EXAMPLE 7

Ascites formation by monoclonal antibody-producing hybridomas

Ascites formation was caused by intraperitoneal inoculation of BALB/c mice intraperitoneally pretreated with 0.5 ml or mineral oil with $1 \times 10^6$ γ 2-11 clone cells capable or producing antibodies having IFN-γ-binding activity. Ten days after intraperitoneal administration of hybridomas, the ascitic fluid was taken and examined for antibody activity until $10^7$-fold dilution. While the antibody activity of the corresponding clone cell culture supernatant was detected until $10^4$-fold dilution, the formation of ascites (ascitization led to an about 1000 times increase in antibody activity.

EXAMPLE 8

Monoclonal antibody purification

Using 4 ml of the ascitic fluid obtained in Example 7 as the starting material, monoclonal antibody purification was performed by the method of Staehelin et al. (Journal of Biological Chemistry, vol. 256, page 9750, 1981). Thus, the ascitic fluid was first centrifuged at 10,000 rpm for 15 minutes to remove fibrin-like substances therefrom and then diluted with phosphate buffer-saline (PBS: 8.1 mM $NaH_2PO_4$, 1.5 mM $KH_2PO_4$, 2.7 mM KCl, 137 mM NaCl; pH 7.2) to a concentration at which the ultraviolet absorption at 280 nm ($A_{280}$) for said dilution would range from 12 to 14. Thereafter, saturated aqueous ammonium sulfate was added to the sample dilution to a concentration of 47% for the sulfate. The mixture was stirred at 4° C. for 60 minutes to effect salting out and then centrifuged (10,000 rpm, 15 minutes) to give a precipitate. The precipitate was dissolved in 20 mM Tris buffer (pH 7.9) containing 50 mM NaCl and dialyzed against 2 liters of the same buffer.

Two hours later, the dialyzing solution was replaced by a fresh 2-liter portion of the same solution and the dialysis was continued for further 15 hours. Thereafter, the precipitate was removed by centrifugation at 10,000 rpm for 15 minutes, and the supernatant was adjusted to a concentration such that the $A_{280}$ value became 20-30. This sample was subjected to fractionation on a DEAE-cellulose column (8 ml, Whatman $DE_{52}$) equilibrated with a sufficient amount of Tris buffer (ph 7.9) containing 50 mM NaCl, elution being made with Tris buffer containing 50 mM NaCl at a flow rate of 1.5 ml/minutes. Under these conditions, the antibody activity was detected mainly in effluent fractions. Antibody confirmation was made by SDS-poly-acrylamide gel electrophoresis (SDS-PAGE) method as described by Laemmli et al. (Nature, vol. 227, page 680, 1970). Thus, some of the fractions obtained by ammonium sulfate salting out and DEAE-cellulose fractionation were each subjected to reduction with 2-mercaptoethanol, followed by 17% SDS gel electrophoresis at 30 volts for 24 hours. In agreement with the antibody activity peaks, two bands were noted at positions corresponding to molecular weights of about 55 kilodaltons (H chain) and about 28 kilodaltons (L chain). The thus-purified antibody fraction 17 was examined for IFN-$\gamma$-binding activity by adding IFN-$\gamma$ (2200 U/ml). It was thus found that about 50% of IFN-$\gamma$ was bound to the antibody (Table 4).

TABLE 4

| Sample | Dilution | Residual IFN activity (U/ml) |
|---|---|---|
| $\gamma$2-11.1 fraction 17 | $10^{-1}$ | 1100 |
| | $10^{-2}$ | 1100 |
| | $10^{-3}$ | 2200 |
| | $10^{-4}$ | 2200 |
| Anti-IgE monoclonal antibody | $10^{-1}$ | 2200 |
| | $10^{-2}$ | 2200 |
| | $10^{-3}$ | 2200 |
| | $10^{-4}$ | 2200 |

EXAMPLE 9

Subclass to which monoclonal antibodies belong

The fraction 17 purified by the method of Example 8 was diluted 10 times and subjected to agar precipitation reaction (Ouchterlony test: Immunological Methods, Gel-Diffusion Technique, Blackwell, Oxford, 1964) using goat anti-mouse IgG1, G2a, G2b and G3 antibodies (Miles) so the IgG subclass to which $\gamma$2-11.1 monoclonal antibodies might belong could be identified. A single distinct band was found between the monoclonal antibody and the goat anti-mouse IgG2b antibody, while no band formation was noted between the monoclonal antibody and other anti-antibodies. Accordingly, said monoclonal antibody was found to belong to IgG2b (Table 5).

TABLE 5

| | Monoclonal antibody subclass | |
|---|---|---|
| Antigen | Antibody | Precipitation curve |
| Monoclonal antibody of the present invention (fraction 17) | Anti-IgG1 | — |
| Monoclonal antibody of the present invention (fraction 17) | Anti-IgG2a | — |
| Monoclonal antibody of the present invention | Anti-IgG2b | + |

TABLE 5-continued

| | Monoclonal antibody subclass | |
|---|---|---|
| Antigen | Antibody | Precipitation curve |
| (fraction 17) Monoclonal antibody of the present invention (fraction 17) | Anti-IgG3 | — |

EXAMPLE 10

Twenty-five ml (65.3 mg) of the monoclonal antibody from the effluent fractions as purified by the procedure of Example 8 was dialyzed overnight against 0.1M $NaHCO_3$ (pH 8.3). Separately, 25 ml of AFFI-GEL 10 (Bio-Rad) was thoroughly washed with water using a glass filter, suspended in 0.1M $NaHCO_3$ (pH 8.3) and mixed with the above antibody. The mixture was stirred gently at 4° C. for 4 hours to effect the reaction, and then allowed to stand at 4° C. overnight. The AFFI-GEL 10 was washed well with 0.1M $NaHCO_3$ (pH 8.3) using a glass filter. To the gel was added 25 ml of a solution (pH 8.0) containing 0.1M ethanolamine and 0.15M NaCl. The mixture was shaken at 4° C. for an hour so as to block possibly remaining unreacted active groups. Then, the gel was washed well with PBS, and suspended in 25 ml of 0 1% $NaN_3$-containing PBS. The suspension was stored at 4° C. Based on the amount of the added antibody and the amount of the antibody in the recovered filtrate, it was found that the antibody was conjugated to the gel in a proportion of 2.35 mg/ml of gel. A column was packed with the reaction product obtained in this manner and used as an antibody column.

EXAMPLE 11

All purification steps were carried out at 4° C. Frozen cells (25 g) were suspended in three volumes (75 ml) of ·7M guanidine-HCl (pH7). The mixture was stirred for 1 h and then centrifuged for 1 h at 30,000 × g. The supernatant was diluted 10-fold with Dulbecco's phosphate buffered saline (PBS) or 0.15M sodium borate buffer (pH9.5) and then centrifuged for 30 min. at 30,000 × g. Alternatively, frozen cells (25 g) were suspended in 1.5 volumes (37.5 ml) of 0.15M sodium borate buffer (pH9.5) and stirred for 1 h. The mixture was sonicated 5 times for 30 seconds and then centrifuged for 1 h at 30,000 × g. The supernatants from either guanidine.HCl extraction or sonification were mixed for 1 h on a rotating shaker with 25 ml silica (NuGel-952AC, Separation Industries, Metuchen, N.J.), prewashed with phosphate buffered saline. The mixture was poured onto an empty column and the column was washed with 20-30 column volumes of 1M NaCl. The column was then eluted with 0.5M tetramethylammonium chloride in 0.01M sodium borate buffer (pH8.0). Interferon activity was eluted in about 200 ml and separated into 4 pools. Each pool was loaded onto a monoclonal antibody (MO $\gamma$ 2-11.1) affinity column (4 ml bed volume) equilibrated with phosphate buffered saline. After washing with 10 column volumes of phosphate buffered saline buffer, the column was eluted with either 1M guanidine-HCl or 50% ethylene glycol containing 1M NaCl and 20 mM sodium phosphate buffer (pH7.0). Interferon activity was eluted in the first 20 ml.

Sodium dodecyl sulfate-polyacrylamide gel electrophoresis was performed as described by Laemmli (reference 9). Protein was determined by fluorescamine analysis with crystalline bovine serum albumin as the reference standard. Interferon activity was determined by the cytopathic effect inhibition assay with vesicular stomattis virus and human WISH cells as reported in reference 10. All interferon titers are expressed in reference units/ml calibrated against the reference standard of partially purified human immune interferon.

A summary of the extraction purification procedure is presented in Table 6. The overall recovery was 25-32% and the purification was about 100 to 769 fold with an average specific activity of about $1-10^7$ units/mg. Total yield of rIFN-gamma was 3-4 times higher with guanidine extraction (Table 6). Sodium dodecyl sulfate-polyacrylamide gel electrophresis of the last stage of purification is shown in FIG. 1. The material purified from guanidine extraction showed a single band at about 18,000 daltons (18K rIFN-γ) whereas the sonification procedure yielded a major band at about 15,000 daltons (15K rIFN-γ) and a minor band at about 17,000 daltons (FIG. 1A). Dimers and oligomers of rIFn-γ were formed (FIG. 1B) on non-reducing gel.

Figure 2:
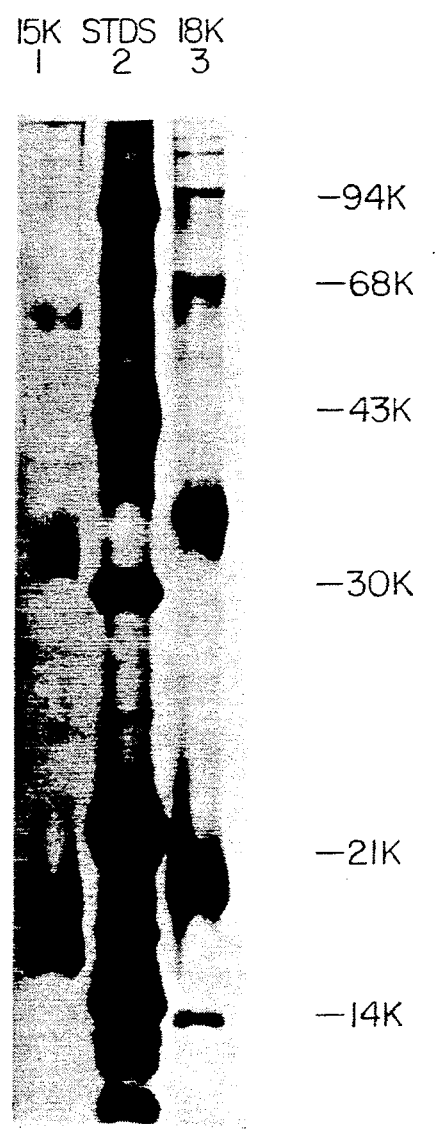
FIG. 2 illustrates the comparison between the predicted amino acid sequence of recombinant human immune interferon and the actual DNA sequence of the 15K and 18K rIFN-γ species.

The 18K rIFN-γ was homogeneous and the amino acid composition was consistent with that predicted from the DNA sequence (see Table 7). Amino acid composition of the 15K and 18K rIFN-γ are given in Table 7. Several hundred picomoles of reduced and carboxymethylated 15K and 18K protein underwent Edman degradation in an automatic gas-phase protein/peptide sequencer. The amino acid N-terminal sequences of first 32 residues and 25 residues of, respectively, 15K and 18K proteins were in accord with that predicted by the DNA sequence (FIG. 2). $^{14}$C-Carboxymethylated cysteines were detected in the first and third cycles of sequence analyses. No N-terminal methionine was detected. N-terminal sequence analysis of the 18K and 15K rIFN-γ demonstrated that the sequence of the area of both proteins is identical to that predicted from the DNA sequence. The C-terminal peptides have also been characterized to determine whether any deletions or changes are present in this region. Amino acid analysis of carboxypeptidase A (CPA) digestion mixture indicated that serine and/or glutamine (C-terminal amino acids) were released from the 18K rIFN-γ, whereas the 15K rIFN-γ was not digested by CPA under the same condition. Since Ser-Gln was the C-terminal sequence or rIFN-γ the 18K species appeared to have the intact C-terminal residues predicted from the DNA sequence and the 15K species has a different C-terminal residue (Lys) which is not cleaved by CPA.

The C-terminal residues predicted from the DNA sequences were further confirmed by analyzing and sequencing the C-terminal peptides after CNBr treatment. C-terminal peptides were separated on the HPLC C-18 reverse-phase column (FIG. 3). A sharp peptide peak (peak II), eluted from the early part of the gradient, was obtained from the 15K rIFN- γ and this peptide was absent from the CNBr digestion mixture of the 15K rIFN-γ. Amino acid analysis of this peptide indicated that this peptide has no homoserine or homoserine lactone and therefore must be the C-terminal CNBr peptide of the 15K protein (Table 8). Based on amino acid analysis (Table 8), this peptide corresponded to the amino acid residues No. 121-131 (no arginine was detectable). The sequence of the 11 amino acids was confirmed by sequence analysis. In the case 18K rIFN-γ, a relatively broad peak was obtained in the early part of the elution. This peak was further separated into two peaks by a shallow gradient. The amino acid analyses indicated that the first peak is the CNBr C-terminal peptide of the 18K protein (Table 8) and the amino acid composition matches the amino acid residues No. 138-146. The sequence of the 9 amino acids was verified by sequence determination. The C-terminal amino acid on the 15K protein was determined to be lysine.

These results indicated that the 18K species was the intact rIFN-γ molecule, whereas the 15K species was a proteolytic product. The peptide bond between amino acid residues No. 131 and No. 132 (Lys-Arg) was cleaved on the 15K species.

EXAMPLE 12

Tryptic Peptide Map of 18K rIFN-γ

Figure 4:
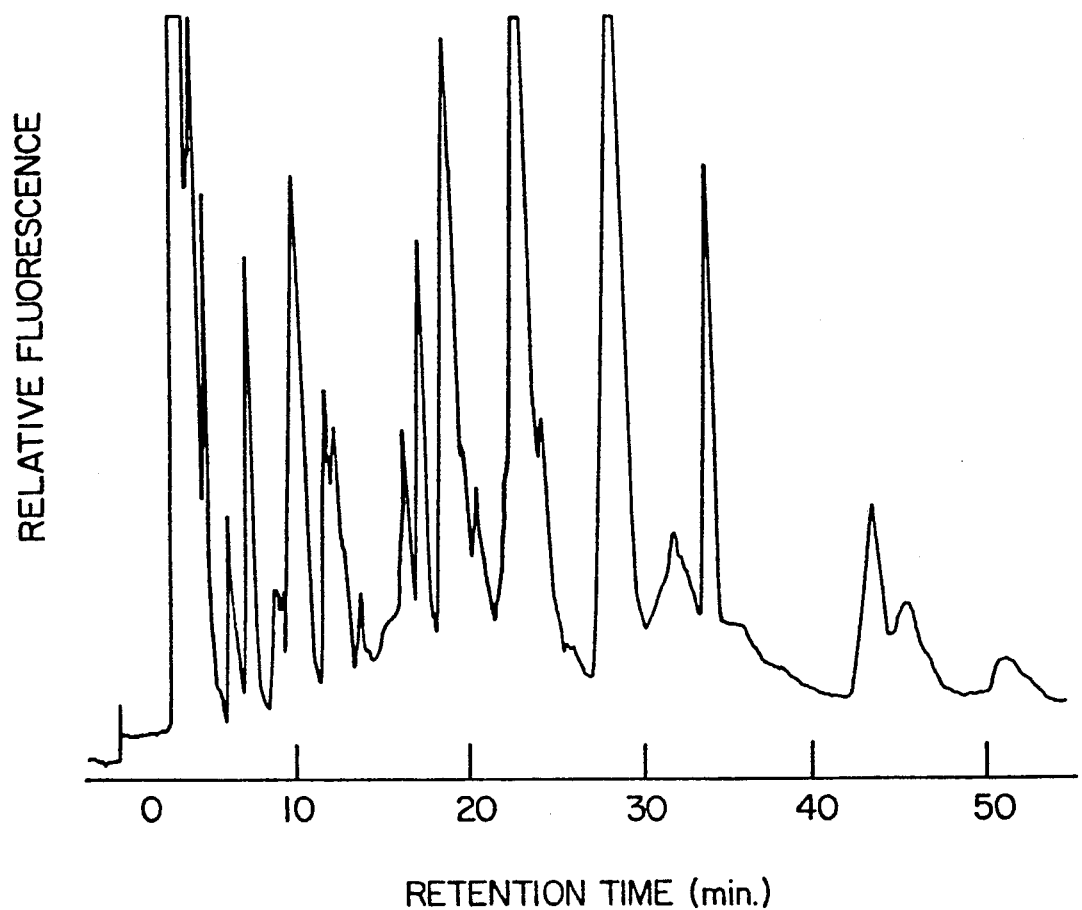
FIG. 4 is a tryptic peptide map of 18K rIFN-gamma.

Tryptic peptide mapping of 18K rIFN-γ was performed. 18K rIFN-γ (43 μg) was digested with TPCK-trypsin (1.1 μg, Worthington (U.S.A.)) at 37° C. for 18 hr in 147 μl of 25 mM ammonium acetate-NaOH (pH 8.0). 2-Mercaptoethanol (0.6 μl ) was added to the digestion mixture and incubation was continued for 2 hr. To stop the reaction, 53 μl of 1% trifluoroacetic acid (TFA) was added. The entire digest sample was chromatographed on an Ultrasphere-octyl column (5 μm, 4.6×250 mm, Altex (U.S.A.) equilibrated with 0.02% TFA - 5% CH$_3$CN. Elution was accomplished at 1.0 ml/min by a linear of 5-70% CH$_3$CN gradient at 30° C. The effluent was monitored by the fluorometric method using fluorescamine. The resulting map is given in FIG. 4.

EXAMPLE 13

C-terminal Amino Acid of 18K rIFN-γ

C-terminal amino acid of 18K rIFN-γ was determined by hydrazinolysis according to the method of Narita et al. (J. Biochem. (Tokyo) 59, 170 (1966)). 18K rIFN-γ (185 μg) was heated at 100° C. for 6 hr with anhydrous hydrazine. The lyophilized hydrazinolysate was dissolved in water, and benzaldehyde was added. The mixture was shaken vigorously for 1 hr at room temperature and then centrifuged. The supernatant was lyophilized and subjected to amino acid analysis. As a result, however, no amino acid was detected. This result is consistent with the fact that the C-terminal amino acid of 18K species is glutamine.

EXAMPLE 14

In accordance with this invention the aforementioned novel immune interferon can be used for the same purposes as the other known interferons, e.g. as a prophylaxis or means for treating viral or neoplastic disorders or as a treatment for immunosupressive conditions. It may be administered in pharmaceutically acceptable oral, injectable or topical composition and modes. Dosage and dose rate may parallel that currently being used in clinical applications of the known interferons, typically about $1-200 \times 10^6$ units daily. These pharmaceutical compositions of the invention contain said immune interferon in association with a compatible pharmaceutically acceptable carrier material. Any conventional carrier material can be utilized. The carrier material can be an organic or inorganic inert carrier material suitable for enteral, percutaneous or parenteral administration. Suitable carriers include water, gelatin, gum arabic, lactose, starch, magnesium stearate, talc, vegetable oils, polyalkylene-glycols, petroleum jelly and the like. Furthermore, the pharmaceutical preparations may contain other pharmaceutically active agents. Additional additives such as flavoring agents, preservatives, stabilizers, emulsifying agents, buffers and the like may be added in accordance with accepted practices of pharmaceutical compounding.

The pharmaceutical preparations can be made up in any conventional form including: a) a solid form for oral administration such as tablets, capsules, pills, powders, granules, and the like; b) a liquid form for oral administration such as solutions, syrups, suspensions, elixirs and the like; c) preparations for parenteral administration such as sterile solutions, suspensions or emulsions; and d) preparations for topical administrations such as solutions, suspensions, ointments, creams, gels, micronized powders, aerosols and the like. The pharmaceutical preparations may be sterilized and/or may contain adjuvants such as preservatives, stabilizers, wetting agents, emulsifiers, salts for varying the osmotic pressure and/or buffers.

Parenteral dosage forms may be infusions or injectable solutions which can be injected intravenously or intramuscularly. These preparations can also contain other medicinally active substances. Additional additives such as preservatives, stabilizers, emulsifying agents, buffers and the like may be added in accordance with accepted practices of pharmaceutical compounding.

TABLE 6

Purification of rIFN-γ

| Purification Step | Total Protein mg | Total Activity units | Specific Activity unit/mg | Purification-fold | Yield % |
|---|---|---|---|---|---|
| I. Guanidine extraction | | | | | |
| Supernatant | 2,806 | $2.5 \times 10^8$ | $9 \times 10^4$ | — | 100 |
| Silica | 98 | $1.0 \times 10^8$ | $1 \times 10^6$ | 11 | 40 |
| Monoclonal Antibody | 8 | $0.8 \times 10^8$ | $1 \times 10^7$ | 110 | 32 |
| II. Sonification | | | | | |
| Supernatant | 6,136 | $8.0 \times 10^7$ | $1.3 \times 10^4$ | — | 100 |
| Silica | 87 | $4.5 \times 10^7$ | $5.2 \times 10^6$ | 400 | 56 |
| Monoclonal Antibody | 2 | $2.0 \times 10^7$ | $1.0 \times 10^7$ | 769 | 25 |

TABLE 7

Amino Acid Compositions of 15K and 18K rIFN-γ

| | | 18K 1-146 (15K predicted value) % 146 | 15K 1-131 (18K predicted value) % 131 |
|---|---|---|---|
| Asp | D | (20) 20.9 | (20) 19.9 |
| Thr | T | (5) 5.1 | (5) 4.9 |
| Ser | S | (9) 9.8 | (11) 6.7 |
| Glu | E | (16) 18.5 | (18) 15.1 |
| Pro | P | (2) (2)* | (2) (2) |
| Gly | G | (4) 5.9 | (5) 5.6 |
| Ala | A | (7) 8.2 | (8) 7.3 |
| Cys | C | (2) (2)* | (2) (2) |
| Val | V | (8) 9.1 | (8) 9.1 |
| Met | M | (3) 4.7 | (4) 3.8 |
| Ile | I | (7) 7.2 | (7) 6.6 |
| Leu | L | (9) 10.5 | (10) 9.6 |
| Tyr | Y | (5) 5.5 | (5) 4.8 |
| Phe | F | (9) 10.3 | (10) 8.2 |
| His | H | (2) 1.8 | (2) 2.5 |
| Lys | K | (19) 19.9 | (20) 16.9 |
| Arg | R | (3) 8.6 | (8) 5.6 |
| W | | (1) (1)* | (1) (1)* |

Figures in parenthesis indicate the predicted residue number from DNA sequence.
*Values for Proline, cystine and tryptophan were not determined.

TABLE 8

| CNBr C-terminal Peptides of 15k and 18K | | |
|---|---|---|
| | 15K | 18K |
| Asp D | | |
| Thr T | 0.9 (1) | |
| Ser S | 1.1 (1) | 0.84 (1) |
| Glu E | 1.1 (1) | 1.1 (1) |
| Pro P | * (1) | |
| Gly G | 1.5 (1) | 1.3 (1) |
| Ala A | 2.4 (3) | 1.1 (1) |
| Cys C | | |
| Val V | | |
| Met M | | |
| Ile I | | |
| Leu L | 1.0 (1) | 1.1 (1) |
| Tyr Y | | |
| Phe F | | 1.0 (1) |
| His H | | |
| Lys K | 1.9 (2) | 2.8 (3) |
| Arg R | | |
| Positions in sequence | 121-131 | 138-146 |

Figures in parenthesis indicate the predicted residue number from DNA sequence.
*Value for Proline was not determined.

REFERENCES

1. Gray, P. W. Et al. (1982) *Nature* 295, 503-508.
2. Staehelin, T. et al. (1981) *J. Biol. Chem.* 256, 9750-9754.
3. Allen, G. Sequencing of Protein and Peptides. (1981) North-Holland Publishing Co., Amsterdam, New York pp. 30-31.
4. Amber, R. P (1967) *Methods in Enzymol.* 11, 436-445.
5. Wolfe, R. A. and Stein, S. (1982) *Modern Methods in Pharmacology* pp. 55-77, Alan R. Liss, Inc. New York, NY.
6. Stein, S. and Brink, L. (1981) *Methods in Enzymology*, 79, 20-25.
7. Hewick, R. M. Hunkapillar, M. W., Hodd, L. E. and Dreyer, W. I. (1981) *J. Biol. Chem.* 256, 7990-7997.
8. Hawke, D., Yuan, P-M., and Shively, J. E. (1982) *Anal. Biochem.* 120, 302-311.
9. Laemmli, U. K. (1970) *Nature* 227, 680-685.
10. Rubinstein, S., Familletti, P. C., and Pestka, S. (1981) *J. Virol.* 37, 755-758.

What is claimed is:

1. An unglycosylated, recombinant human immune interferon having the amino acid sequence:

Cys Tyr Cys Gln Asp Pro Tyr Val Lys Glu Ala Glu
Asn Leu Lys Lys Tyr Phe Asn Ala Gly His Ser Asp
Val Ala Asp Asn Gly Thr Leu Phe Leu Gly Ile Leu
Lys Asn Trp Lys Glu Glu Ser Asp Arg Lys Ile Met
Gln Ser Gln Ile Val Ser Phe Tyr Phe Lys Leu Phe
Lys Asn Phe Lys Asp Asp Gln Ser Ile Gln Lys Ser
Val Glu Thr Ile Lys Glu Asp Met Asn Val Lys Phe
Phe Asn Ser Asn Lys Lys Lys Arg Asp Asp Phe Glu
Lys Leu Thr Asn Tyr Ser Val Thr Asp Leu Asn Val
Gln Arg Lys Ala Ile His Glu Leu Ile Gln Val Met
Ala Glu Leu Ser Pro Ala Ala Lys Thr Gly Lys Arg
Lys Arg Ser Gln Met Leu Phe Arg Gly Arg Arg Ala
Ser Gln, which interferon is essentially free of proteolytic fragments thereof.

2. The immune interferon of claim 1 as a homogenous polypeptide.

3. The immune interferon of claim 1 in which the amino-terminal amino acid residue is methionine.

* * * * *

UNITED STATES PATENT AND TRADEMARK OFFICE
CERTIFICATE OF CORRECTION

PATENT NO. : 5,278,286
DATED : January 11, 1994
INVENTOR(S) : Hsiang-Fu Kung, et. al.

It is certified that error appears in the above-indentified patent and that said Letters Patent is hereby corrected as shown below:

Title page, item [73], Assignee: should read-- and Takeda Chemical Industries, Ltd., Osaka, Japan--.

Signed and Sealed this

Twenty-sixth Day of November 1996

*Attest:*

BRUCE LEHMAN

*Attesting Officer*     *Commissioner of Patents and Trademarks*